United States Patent [19]

Carris

[11] 4,227,522
[45] Oct. 14, 1980

[54] INHALATION DEVICE

[75] Inventor: Milton C. Carris, Cupertino, Calif.

[73] Assignee: Syntex Puerto Rico, Inc., Humacao, P.R.

[21] Appl. No.: 939,615

[22] Filed: Sep. 5, 1978

[51] Int. Cl.³ .................................. A61M 15/00
[52] U.S. Cl. ........................... 128/203.15; 222/636
[58] Field of Search .......... 128/266, 208, 206, 203.15; 222/630, 636, 637

[56] References Cited

U.S. PATENT DOCUMENTS

| | | | |
|---|---|---|---|
| 2,587,215 | 2/1952 | Priestly | 128/208 X |
| 4,013,075 | 3/1977 | Cocozza | 128/266 |
| 4,064,878 | 12/1977 | Lundquist | 128/266 X |

FOREIGN PATENT DOCUMENTS 2804852  8/1978  Fed. Rep. of Germany ........... 128/266

*Primary Examiner*—Henry J. Recla
*Attorney, Agent, or Firm*—Tom M. Moran; Joseph I. Hirsch

[57] ABSTRACT

An inhalation device for dispensing a powdered medicament from a medicament-holding container having a first part which is an elongate housing having a passageway for the movement of air therethrough, one end of the housing being an output end adapted for insertion into the mouth or nasal passage of the user thereof, the passageway terminating in an emptying chamber at the output end of the housing, the cross-sectional area of the passageway being less than the cross-sectional area of the emptying chamber, and means for receiving the second part of the device which is a carriage moveably connected to the first part and having means to receive a medicament-holding container so that when an open end of the medicament-holding container is placed adjacent the inner end of the emptying chamber during inhalation the medicament is dispensed from the container.

10 Claims, 11 Drawing Figures

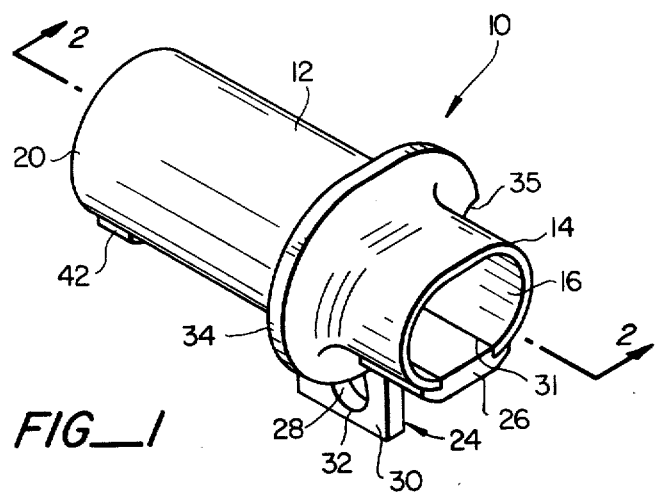
FIG_1
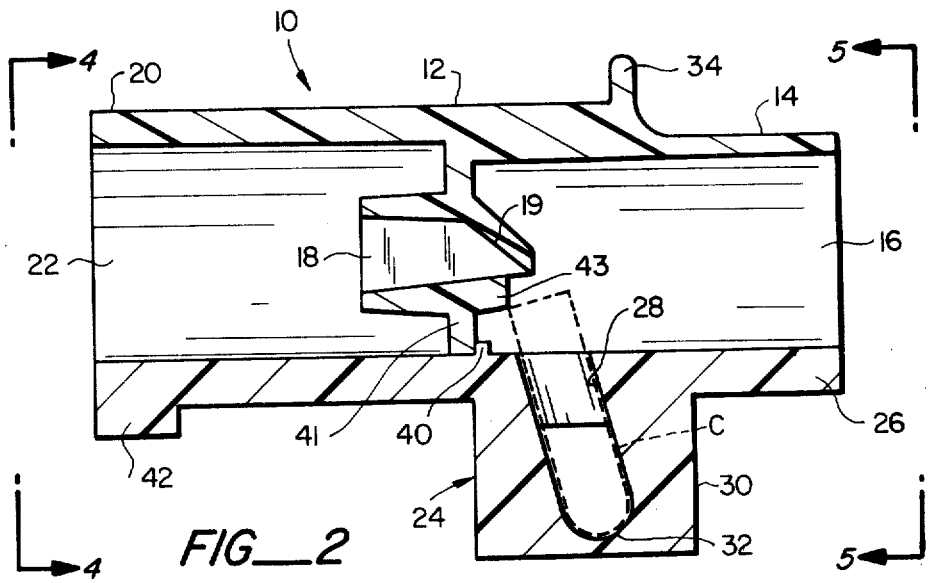
FIG_2
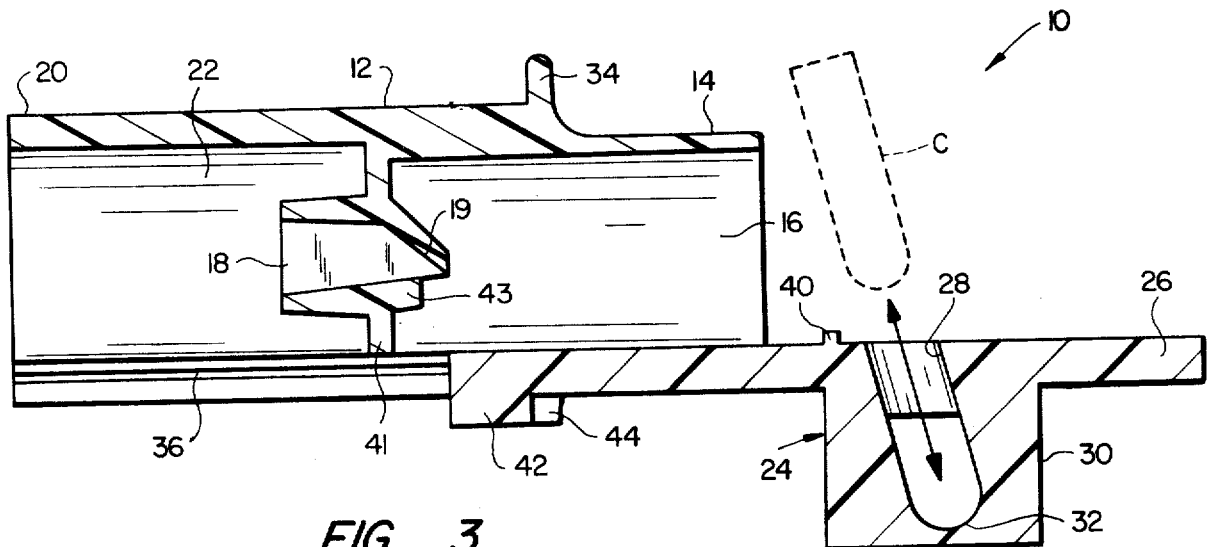
FIG_3

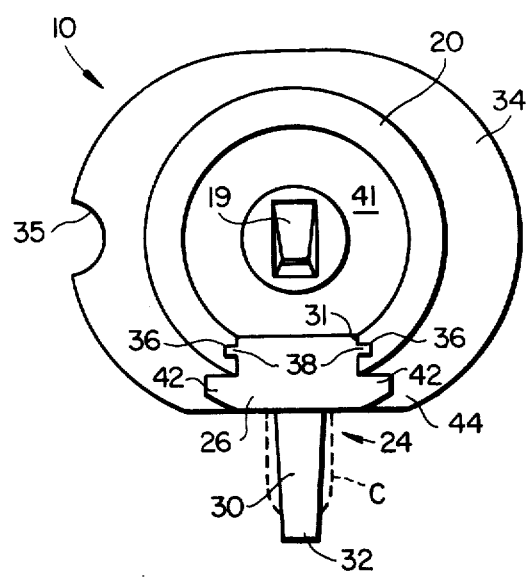
FIG_4
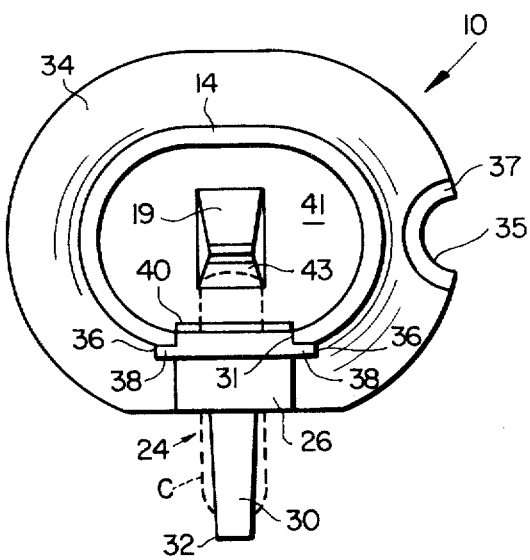
FIG_5
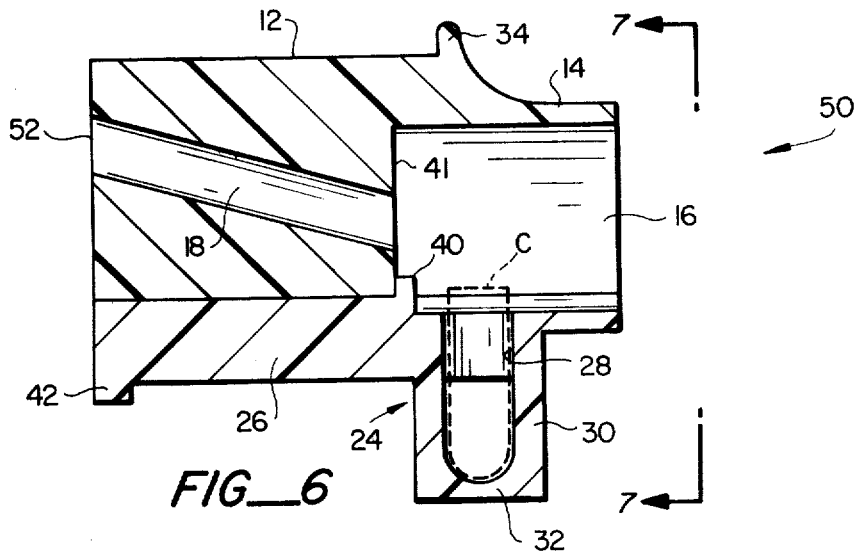
FIG_6
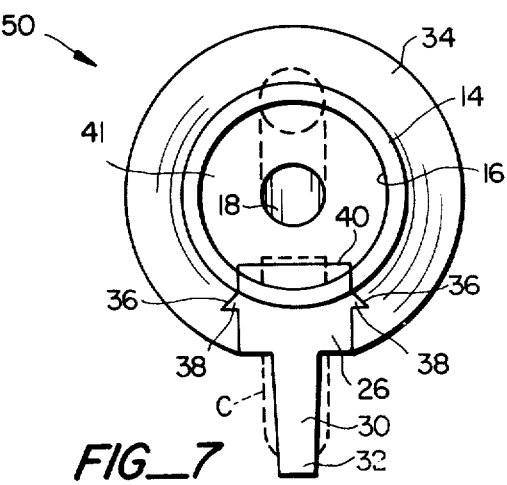
FIG_7

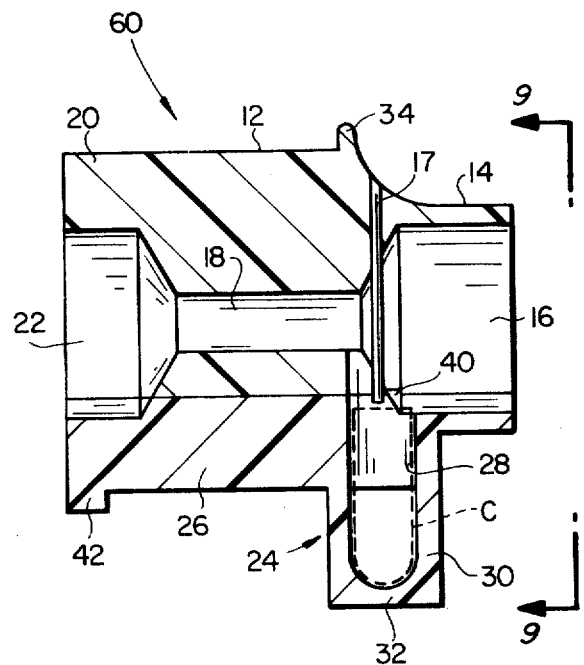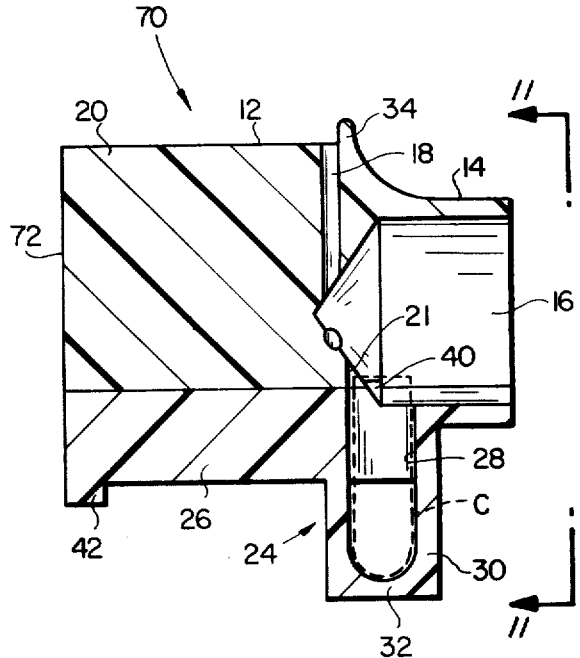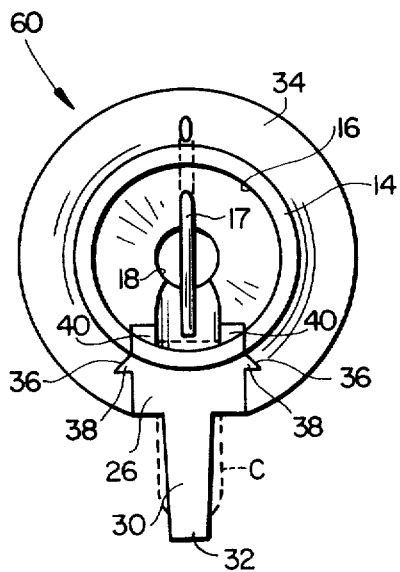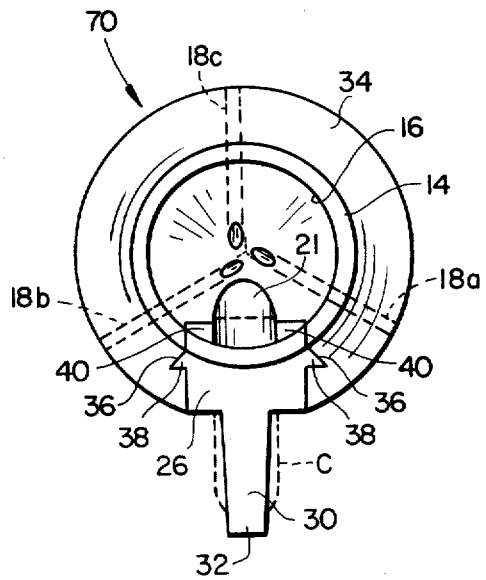
FIG_8  FIG_10  FIG_9  FIG_11

INHALATION DEVICE

FIELD OF THE INVENTION

This invention relates to devices for the administration of powdered medicaments by inhalation. More particularly, this invention relates to two-part inhalation devices having no parts which move while the medicament is actually being dispensed during inhalation. The device is capable of causing a powdered medicament within a container held by the device to be rapidly and effectively dispensed from the container, entrained by the airstream being inhaled and carried to the nose, throat or lungs of the user.

BACKGROUND OF THE INVENTION

Known, prior art inhalation devices include, for example, those shown in U.S. Pat. Nos. 3,938,516; 3,964,483; 3,973,566; and 4,005,711. In all of these devices, a container containing a powdered medicament is inserted into an opening in the device and held by either a friction fit or by the finger pressure of the user. It is sometimes difficult, however, to properly insert, retain and/or withdraw the container (hereinafter generally referred to as the capsule). For example, if the capsule is too small it is not properly retained within the opening, or if it is too big it may be damaged or crushed on insertion. The use of such devices requires that the capsule first be opened (which requires both hands) and then inserted into the opening in the device (also requiring both hands). Thus the device is set down when the capsule is opened and then picked up for placement of the capsule in the opening. This procedure increases the chances of spillage of the powdered medicament.

Other devices have been proposed which employ means for opening the capsule after it is inserted into the inhalation device. See, for example U.S. Pat. No. 4,014,336. However, with these devices there is a possibility that that portion of the capsule removed might remain in the device and adversely affect the delivery of the medicament.

Still other devices are discussed in U.S. Pat. Nos. 1,406,903; 2,587,215; and 2,603,215.

With the instant invention, the chance of accidental spillage is lessened because the capsule is first positioned on the device, and then the top half or cap of the capsule is removed. Further, when properly used, no portion of the capsule will adversely affect delivery of the medicament during inhalation.

SUMMARY OF THE INVENTION

The invention comprises a two-part, breath-actuated inhalation device for dispensing a powdered medicament from a medicament-holding container (e.g., a gelatin capsule). The first part is an elongate housing having a passageway for the movement of air therethrough, one end of the housing being an output end adapted for insertion into the mouth or nasal passage of the user thereof, the passageway terminating in an emptying chamber at the output end of the housing, the cross-sectional area of the passageway being less than the cross-sectional area of the emptying chamber, and means for receiving the second part of the device. The second part of the device comprises means to receive a medicament-holding capsule, which receiving means is moveably connected to the first part so that when an open end of the medicament-holding capsule is placed adjacent the emptying chamber during inhalation the medicament is dispensed from the capsule.

BRIEF DESCRIPTION OF THE DRAWINGS

The foregoing and still further features and advantages of the present invention will become more apparent from the following detailed description, taken together with the accompanying drawings wherein:

FIG. 1 is a perspective view of the inhalation device of the present invention;

FIG. 2 is a longitudinal, vertical cross-sectional view of the inhalation device of FIG. 1 taken along line 2—2 of FIG. 1 showing the device of the invention ready for inhalation;

FIG. 3 is a longitudinal, vertical cross-sectional view of the inhalation device similar to FIG. 2 showing the device ready for insertion or withdrawal of the capsule;

FIG. 4 is a left-hand end view of the device of FIG. 1 taken along line 4—4 of FIG. 2;

FIG. 5 is a right-hand end view of the device of FIG. 1 taken along line 5—5 of FIG. 2;

FIG. 6 is a longitudinal, vertical cross-sectional view of an alternative embodiment of the device of this invention having no air deflector;

FIG. 7 is a right-hand end view of the alternative embodiment of the inhalation device shown in FIG. 6 taken along line 7—7 of FIG. 6;

FIG. 8 is a longitudinal, vertical cross-sectional view of an alternative embodiment of an inhalation device having an additional air passage leading to the capsule;

FIG. 9 is a right-hand end view of the embodiment shown in FIG. 8 taken along line 9—9 of FIG. 8;

FIG. 10 is a longitudinal, vertical cross-sectional view of still another alternative embodiment of an inhalation device of this invention having three passageways in the housing; and FIG. 11 is a right-hand end view of the inhalation device of FIG. 10 taken along line 11—11 of FIG. 10.

FURTHER DESCRIPTION AND PREFERRED EMBODIMENTS

In the discussion below, reference will be made to a capsule as the exemplary container for presenting the medicament to the device for administration, although it is contemplated that other medicament-holding forms would be equally suitable for use with the devices described herein if appropriate structural modifications are made, if needed, to the devices to accommodate the different container or forms.

Referring first to FIG. 1, an inhalation device 10 is shown having an elongated housing 12 which may be cylindrical as shown in FIGS. 4, 7, 9 and 11 or may be eliptical as shown in FIG. 5. Alternatively, part of the housing may be substantially cylindrical while the other part (e.g., the mouthpiece) may be eliptical in cross section as in FIG. 1. At one end of housing 12 is a mouthpiece 14 intended for insertion into the mouth or nasal passage(s) of a user thereof. Mouthpiece 14 can be designed to permit insertion directly into the nasal passages or, if desired, an adaptor (not shown) can be placed over the mouthpiece to permit nasal use. Adjacent mouthpiece 14 is an emptying chamber 16 connected at the inner end thereof to passageway 18 which extends upstream to the inlet end 20 of the device and communicates with inlet chamber 22. The manner of connecting passageways 18 with chamber 16 and chamber 22 can be as shown or more streamlined, if desired, as long as the particular configuration selected is effective to cause the powdered medicament to be expelled from capsule C during the desired number of inhalations. Other exemplary designs for the passageway are shown in FIGS. 6, 8 and 10, and are discussed hereafter. At the downstream end of passageway 18 is deflector 19 which deflects the flow of air, drawn through passageway 18 during inhalation, into a medicament-holding capsule properly positioned adjacent thereto.

The housing 12 may be of such design that the longitudinal axis of passageway 18 and chambers 16, 22 are substantially the same or are parallel. Alternatively, the longitudinal axis of passageway 18 may be slightly tilted, for example at an angle of about 5° to 30°, preferably about 15°, from the longitudinal axis of emptying chamber 16, for example as is best seen in FIG. 6 hereof.

Adjacent the lower, inner end of chamber 16, there are means for receiving a capsule-holding means 24 which releasably holds capsule C. The means for receiving the capsule-holding means is shown as an elongated slot 31 in the bottom of housing 12 into which the capsule-holding means is slideably received. The capsule-holding means is a carriage which comprises an upper part 26 which has a receiving chamber 28 located therein into which capsule C fits. As shown, chamber 28 is tilted at an angle of about 5° to 30°, generally about 15°, toward the upstream end of the device. Integral with upper portion 26 is a lower extension 30. The chamber 28 does not extend all the way through the lower extension 30, but is designed so that capsule C is supported by the lower most portion 32 of extension 30. The carriage is supported within slot 31 by cooperating grooves 36, in the portion of the housing adjacent the slot, and tongues 38 on the carriage which fit into, and are slidably received by, grooves 36, as is best seen in FIGS. 4 and 5. The grooves 36 extend the entire length of slot 31 and permit, in conjunction with tongues 38, the carriage to move longitudinally relative to the upper portion of the housing. When the carriage is positioned as shown in FIG. 2, i.e., with the capsule positioned ready for inhalation, internal stop 40 on the top middle portion of the carriage contacts flange 41 depending from the structure which defines passageway 18 to stop the upstream longitudinal movement of the carriage to position chamber 28 with the capsule held therein at the appropriate position for inhalation. Movement of the carriage toward the capsule insertion or removal position, i.e., as shown in FIG. 3, is limited by contact of stop 42 with a lower portion 44 of collar 34. In addition, this limits the separation of the carriage from the remainder of the inhalation device. Capsule stop 43 also helps to position the capsule adjacent deflector 19 such that air, drawn through passageway 18 upon inhalation, is deflected into a properly positioned capsule.

FIGS. 4 and 5 show that lower extension 30 is of smaller cross-sectional dimension than the upper portion 26 of the receiving means 24. As stated previously, extension 30 is of such dimension that a portion 32 thereof will support capsule C as shown. However, the width of extension 30 which extends perpendicular to the longitudinal dimension of upper part 26 is less than the diameter of capsule C. Thus, capsule C extends slightly beyond at least one side of extension 30, and preferably extends beyond both sides of extension 30 (for example as shown in FIGS. 4 and 5). When the user wishes to remove capsule C from chamber 28, carriage 24 is moved to the position shown in FIG. 3, the user places a thumb and forefinger on either side of extension 30 in contact with a capsule therein, and pushes upwardly thus moving the capsule in the upward direction as shown in FIG. 3 where it can be grasped with the other hand and removed. Thereafter, a new capsule can be placed in chamber 28 for subsequent use.

The inhalation device is equipped with collar 34 which extends around the periphery of the outside of the device. The collar is designed to prevent the patient from inhaling the entire device, to provide proper placement of the device in the user's mouth, and also to provide a stop for the capsule receiving means, as discussed hereinbefore.

In Addition collar 34 may have a notch 35 therein which has a cross-section which is of sufficient size to allow the smaller part of a two-part capsule to fit therein, but which is too large to allow the other, larger part, not shown, to fit therein or be pulled therethrough. Thus, when a user of the device wishes to open a capsule, he or she places the edge of the larger part of the two-part capsule against flat surface 37 adjacent notch 35 and pulls to separate the two capsule parts. This is more fully described in copending application Serial No. (PA-918), filed concurrently herewith, and which is incorporated herein by reference to the extent necessary to complete, or render fully understandable, the disclosure of this aspect of the devices described herein.

Thus, in operation, FIG. 3 shows the device as it is ready to be loaded with capsule C by manual placement thereof into chamber 28. Once the capsule is placed into chamber 28, the housing is held in one hand, and the carriage is pushed relative to the housing 12 until stop 40 contacts flange 41 and the top edge of capsule C comes close to, or contacts, stop 43 to properly position the capsule adjacent deflector 19. The user then places the mouthpiece 14 in his or her mouth and inhales. Air enters chamber 22, passes through passageway 18 until it hits deflector 19 where at least a portion of the air stream is deflected into capsule C holding the powdered medicament. The deflector can be placed at different positions and at different angles, etc., provided a sufficient portion of the air stream is deflected into the capsule to cause the powdered medicament to be dispensed therefrom. Upon inhalation, the air passing through the device, including the portion deflected into the capsule, promptly and effectively causes the powdered medicament to be expelled from the capsule and entrained in the flowing airstream and, as such, carried into the throat, nasal passages or lungs of the user for beneficial or therapeutic action thereof to occur.

Other alternative embodiments useful as inhalation devices are shown in FIGS. 6–11, wherein like numerals refer to like parts. In the inhalation device 50 of FIGS. 6 and 7, housing 12 encompasses a passageway 18 and an emptying chamber 16 enclosed by mouthpiece 14. The longitudinal axis of the passageway 18 is shown as being slightly tilted (an angle of about 5° to 30°, preferably about 15° as shown), but may also be essentially parallel to the overall longitudinal axis of the device. Chamber 28 in capsule receiving means 24 may be perpendicular to the longitudinal axis as shown in FIGS. 6 and 7 or at a slight angle as shown in FIG. 3, however, it is generally not necessary to tilt both the passageway and the chamber, although this can be done if desired and the particular angles of tilt are chosen so as to achieve the desired medicament dispensing. The construction and operation of the device having the design of FIGS. 6 and 7 differs from that of FIGS. 1–5 in that there is no deflection means 19 between passageway 18 and chamber 16, but otherwise is similar in operation. The carriage or capsule holding means 24 has chamber 28 for receiving capsule C which contains the powdered medicament. The carriage 24 moves relative to housing 12 by tongues 38 sliding in grooves 36, with stop 40 preventing upstream movement by contact with flange 41 and stop 42 preventing downstream movement of carriage 24 by contact with lower part 44 (not shown) of collar 34. In use, the patient moves the carriage to the position analagous to that of FIG. 3, inserts the medicament-holding capsule into chamber 28, and moves the carriage to the position as shown in FIG. 6. The patient then places mouthpiece 14 in his or her mouth and inhales. Air enters passageway 18 at the entry end 52, passes into emptying chamber 16 whereat, because of the angular relationships of the passageway and the chamber, a portion of the air goes into capsule C to empty the medicament into the moving air stream such that it is carried into the throat, nasal passages or lungs for the beneficial or therapeutic action thereof to occur.

Still another embodiment is shown in FIGS. 8 and 9 when like numerals are, once again, utilized to represent like elements as previously described. Here, in addition to the passageway 18 which allows air to traverse the length of device 60, there is an additional passageway 17 which is perpendicular to the longitudinal axis of passageway 18. In this case, when the patient inserts the mouthpiece 14 of the device into his or her mouth and inhales, air enters through passageway 18 into emptying chamber 16 and at the same time air is drawn through passageway 17 to impinge upon the powder which is held in capsule C. This air being drawn through passageway 17 additionally assists in dispensing the powder into the air stream flowing through chamber 16.

In still another alternative embodiment, shown in FIGS. 10 and 11, passageway 18, as represented by cooperating passageways 18a, 18b and 18c, is substantially perpendicular to the longitudinal axis of the device 70. In this case when the patient inserts the mouthpiece 14 into his or her mouth and inhales, air is drawn through passageways 18a, 18b and 18c and impinges upon surface 21. As is best seen in FIG. 11, the longitudinal axes of passageways 18a, 18b and 18c are off-set with respect to the longitudinal axis of emptying chamber 16. In particular, as shown in FIG. 11, the extensions of the left-hand edges of the passageways intersect along the longitudinal axis of the emptying chamber. By offsetting the axes of the passageways in this manner, turbulent air flow is created in emptying chamber 16 during inhalation, a component of which is directed into or enters chamber 28 adjacent the lower, inner end of chamber 16 and any capsule which may be held therein. During inhalation, air drawn through passageways 18a, 18b and 18c and emptying chamber 16 causes the powdered medicament to be expelled from the capsule, entrained in the air flowing through the device, and carried into the nose, throat or lungs of the user where beneficial action of the medicament occurs. In this particular embodiment, it is contemplated that the passageways can be angled toward the remote end 72 of the device and/or chamber 28 can be tilted (up to about 40°) toward the passageways (i.e., toward end 72) to further assist in causing the powdered medicament to be expelled from the capsule.

The entire device can be made of metal but preferably is made of suitable plastic material such as nylon, polyacetal or polypropylene. With the exception of the capsule or other medicament holding container each part of the device in the basic elements is preferably of unitary construction, although multi-piece construction is also contemplated. The device of this invention can be manufactured quite readily by milling or preferably by injection molding using means well known in the art, thereby effecting substantial cost reduction of the manufacturing process, without adversely affecting the medicament administration inhalation.

The physical properties of each medicament formulation (i.e., the ability to fluidize and the flow characteristics thereof) will affect the case or manner in which it is dispensed with these or other inhalation devices. However, for a given powdered formulation, varying the diameter of passageway 18, the positioning of chamber 28 (from the position as shown toward the open end of chamber 16), the angle of the deflector 19, the depth of which the deflector 19 extends above or below the longitudinal axis of passageway 18, the height above the inside of emptying chamber 16 top which the medicamentholding container extends, and/or, in general, modification of the overall configuration and shape of chamber 16 and passageway 18, devices can be made to deliver the medicament in a different number of inhalations or in a longer or shorter period of time, depending upon the nasal or lung capacities and strengths of each particular user. Quite obviously, no single device will be optimal for all persons requiring administration of powdered medicaments since, for example, people with differing lung capacities and strengths are known to generate flow rates from about 30 liters/minute or so to about 120 liters/minute or so through inhalation devices of this and known types. Nonetheless, the devices of this invention afford such variability through proper selection of the various design parameters listed above, that a device, embraced within the scope of this invention, can be designed for a particular patient-generated flow rate to deliver the medicament according to a certain set of pre-determined objectives (e.g., slow or fast administration, one or more inhalations, etc.). The net result is that a family of devices, all embraced within the present invention, can be designed, each of which will deliver the medicament under a different, given set of selected administration conditions. Conversely, the devices of this invention can be designed to cover an extensive range of operating conditions and thus be suitable for use by a variety of persons having differing inhalation capabilities or capacities.

While the present invention has been described with reference to specific embodiments thereof, it will be understood by those skilled in this art that various changes may be made and equivalents may be substituted without departing from the true spirit and scope of the invention. Additionally, other modifications may be made to adapt a particular situation, material or composition of matter, structural desirability, or then-present objective to the spirit of this invention without departing from its essential teachings.

The subject matter claimed is:

1. A two-part breath-actuated inhalation device for dispensing a powdered medicament from a powdered medicament-holding container, the first part of said device comprising an elongate housing having a passageway for the movement of air therethrough, one end of said housing being an output end adapted for insertion into the mouth or nasal passage of a user thereof, the passageway having an inlet end terminating in an emptying chamber at said output end of said housing, the cross-sectional area of the passageway being less than the cross-sectional area of the emptying chamber, and means for receiving the second part of said device, said receiving means being an elongate slot extending along the bottom portion of said housing, the slot being defined by two sides of said housing parallel to the longitudinal axis thereof;

said second part of said device comprising means to receive the medicament-holding container, said medicament-holding container receiving means adapted to be slidingly received by said slot so that when a medicament-holding container having only one open end is placed into said medicament-holding container receiving means in said second part and said two parts are moved longitudinally relative to each other, the open end of the medicament-holding container will be positioned adjacent the inner end of the emptying chamber, whereby during inhalation, a component of air flowing through the passageway flows into the medicament-holding container to dispense the medicament therefrom.

2. The device of claim 1 wherein said medicament-holding container receiving means comprises a carriage slidably engaged within said slot and has longitudinal sides complementary to the longitudinal sides of said housing to allow said carriage to be moved parallel to the longitudinal axis of said housing, said carriage having a chamber therein for receiving a medicament-holding container when said carriage is in a first container-receiving position, whereby when said carriage is moved to a second position where the open end of a medicament-holding container is adjacent the inner end of the emptying chamber and when air is drawn through said device a component of the air flowing through the passageway during inhalation dispenses the medicament from the medicament-holding container.

3. The device of claim 1 wherein said means for receiving said second part is a slot extending the length of said housing along the bottom portion thereof, the slot being defined by two sides of said housing parallel to the longitudinal axis thereof, and said medicament-holding container receiving means comprises a carriage being substantially the same length as said housing, being slidably engaged within the slot in said first part, and having longitudinal sides complementary to the longitudinal sides of the slot in said first part to allow said carriage to be moved parallel to the longitudinal axis of said housing, said carriage having a chamber therein for releasably receiving a powdered medicament-holding container when in a first container-receiving position, said carriage being adapted to be moved within the slot to a second position where the open medicament-holding container is adjacent the inner end of the emptying chamber, such that during inhalation with said carriage in the second position a component of the air flowing through the passageway serves to dispense the medicament from the medicament-holding container.

4. The device of claim 3 wherein said carriage has an extension depending from the lower portion thereof, the chamber for receiving the medicament-holding container extends into said extension, the container-receiving chamber being partially open along at least one side thereof such that a medicament-holding container can be at least partially removed from the container-receiving chamber by application of finger pressure to the exposed side of the container positioned within the chamber.

5. The device of claim 4 wherein two opposed sides of said extension are open so that the container may be forced at least part way out of the chamber by application of finger pressure by the user to the container-receiving container through the openings.

6. The device of claims 1, 3 or 4 further including stop means for preventing said carriage from being totally separated from said housing.

7. The device of claims 1, 3 or 4 further including means extending into the emptying chamber adjacent the interface thereof with the passageway and transversely thereto a distance into the projected air flow path of the air stream exiting from the passageway for deflecting at least a portion of the air being drawn through the passageway during inhalation into an open, medicament-holding container held within the chamber adjacent thereto and transversely to the longitudinal axis of said device.

8. The device of claim 1, 3 or 4 further including means extending into the emptying chamber adjacent the interface with the passageway and transversely thereto a distance into the projected air flow path of the air stream exiting from the passageway for deflecting at least a portion of the air being drawn through the passageway during inhalation into an open medicament-holding container, the longitudinal axis of the container-receiving chamber being at an angle of about 5°-30° with respect to the longitudinal axis of the passageway so that the mouth of the container-receiving chamber and the passageway are directed toward each other.

9. A two-part breath-actuated inhalation device for dispensing a powdered medicament from a powdered medicament-holding container having only one open end, said first part of said device comprising an elongate housing having a passageway for the movement of air therethrough, one end of said housing being an output end adapted for insertion into the mouth or nasal passage of a user thereof, the passageway having an inlet end terminating in an emptying chamber at said output end of said housing, the cross-sectional area of the passageway being less than the cross-sectional area of the emptying chamber, means extending into the emptying chamber adjacent the interface thereof with the passageway and transversely thereto a distance into the projected air flow path of the air stream exiting from the passageway for deflecting at least a portion of the air being drawn through the passageway during inhalation into an open, medicament-holding container held adjacent thereto, and an elongate slot extending along the bottom portion of said housing, the slot being defined by two sides of said housing parallel to the longitudinal axis of thereof and adapted for receiving said second part of said device;

said second part of said device comprising a carriage for receiving the medicament-holding container, said carriage slidably engaged within the slot and having longitudinal sides complementary to said two sides of said housing defining the slot to allow said carriage to slide parallel to the longitudinal axis of said housing, said carriage having a chamber therein for releasably receiving a medicament-holding container when in a first container-receiving position, said carriage being adapted to be moved within the slot to a second position where the open, medicament-holding container is adjacent the inner end of the emptying chamber, said carriage having an extension depending from the lower portion thereof in which the container-receiving chamber extends, the container-receiving chamber being partially open along opposed sides thereof such that a medicament-holding container can be at least partially removed from the container-receiving chamber by application of finger pressure to the exposed sides of a container positioned within the container-receiving chamber, said carriage further having stop means thereon for preventing said carriage from being totally separated from said housing, whereby when said carriage is moved to the first position a medicament-holding container can be placed within the container-receiving chamber, and, when said carriage holding a medicament-holding container within the container-receiving chamber is moved to the second position where the longitudinal axis of said chamber is transverse to the longitudinal axis of said device, air being drawn through the passageway during inhalation and being deflected by said deflector means into the medicament-holding container through said open end causes the powdered medicament to be dispensed therefrom.

10. The device of claim 9 wherein the longitudinal axis of the container-receiving chamber is at an angle of about 5°–30° with respect to the longitudinal axis of the passageway such that the mouth of the container-receiving chamber and the passageway are directed toward each other.

* * * * *